(12) United States Patent
Qing-Qing et al.

(10) Patent No.: US 9,649,408 B1
(45) Date of Patent: May 16, 2017

(54) SYSTEMS AND METHODS FOR STERILIZATION OF BONE OR BONE COMPONENTS

(75) Inventors: Qiu Qing-Qing, Branchburg, NJ (US); Jerome Connor, Doylestown, PA (US)

(73) Assignee: LifeCell Corporation, Branchburg, NJ (US)

( * ) Notice: Subject to any disclaimer, the term of this patent is extended or adjusted under 35 U.S.C. 154(b) by 405 days.

(21) Appl. No.: 12/939,629

(22) Filed: Nov. 4, 2010

Related U.S. Application Data

(60) Provisional application No. 61/258,487, filed on Nov. 5, 2009.

(51) Int. Cl.
*A61F 2/00* (2006.01)
*A61L 27/54* (2006.01)

(52) U.S. Cl.
CPC .................................. *A61L 27/54* (2013.01)

(58) Field of Classification Search
USPC ......................................................... 424/423
See application file for complete search history.

(56) References Cited

U.S. PATENT DOCUMENTS

| | | | |
|---|---|---|---|
| 5,213,619 A * | 5/1993 | Jackson et al. | 134/1 |
| 5,336,616 A | 8/1994 | Livesey et al. | |
| 5,788,661 A | 8/1998 | Jupuntich | |
| 6,933,326 B1 | 8/2005 | Griffey et al. | |
| 7,108,832 B2 | 9/2006 | Christensen et al. | |
| 7,358,284 B2 | 4/2008 | Griffey et al. | |
| 7,560,113 B2 | 7/2009 | Christensen | |
| 7,771,652 B2 | 8/2010 | Christopher et al. | |
| 2003/0143207 A1 | 7/2003 | Livesey et al. | |
| 2005/0028228 A1 | 2/2005 | McQuillan et al. | |
| 2005/0268573 A1 | 12/2005 | Yan | |
| 2005/0281856 A1 * | 12/2005 | McGlohorn et al. | 424/423 |
| 2006/0073592 A1 | 4/2006 | Sun et al. | |
| 2007/0092398 A1 * | 4/2007 | McDonald | A61L 2/206 422/28 |
| 2007/0110820 A1 * | 5/2007 | Behnam | 424/549 |
| 2007/0248575 A1 | 10/2007 | Connor et al. | |
| 2008/0027542 A1 | 1/2008 | McQuillan et al. | |
| 2008/0240981 A1 | 10/2008 | Berentsveig et al. | |
| 2009/0035289 A1 | 2/2009 | Wagner et al. | |
| 2009/0306790 A1 | 12/2009 | Sun | |
| 2010/0040687 A1 | 2/2010 | Pedrozo et al. | |
| 2010/0137677 A1 | 6/2010 | Friedman et al. | |
| 2010/0137817 A1 | 6/2010 | Hardman et al. | |
| 2010/0161054 A1 | 6/2010 | Park et al. | |
| 2010/0196905 A1 | 8/2010 | McNulty et al. | |
| 2010/0209408 A1 | 8/2010 | Stephen et al. | |
| 2010/0272782 A1 | 10/2010 | Owens et al. | |

FOREIGN PATENT DOCUMENTS

WO     WO 2009150488     12/2009

OTHER PUBLICATIONS

Qiu et al., "Inactivation of Bacterial Spores and Viruses in Biological Material Using Supercritical Carbon Dioxide With Sterilant," *Journal of Biomedical Materials Research Part B: Applied Biomaterials* 2009 p. 572-578.
White et al., "Effective Terminal Sterilization Using Supercritical Carbon Dioxide," *Journal of Biotechnology* 2006, p. 1-12.
U.S. Appl. No. 12/939,669, Leamy et al.
Eckert, Charles A. et al., "Supercritical fluids as solvents for chemical and materials processing", *Nature*, vol. 383, Sep. 26, 1996, pp. 313-318.
Jessop, Phillip G. et al., "Homogeneous catalytic hydrogenation of supercritical carbon dioxide", *Nature*, vol. 368, Mar. 17, 1994, pp. 231-233.
Poliakoff, Martyn et al., "A supercritical success story", *Chemistry & Industry*, Oct. 4, 1999, pp. 750-752.
Poliakoff, Martyn et al., "Intermediates in organometallic and organic chemistry: spectroscopy, polymers, hydrogenation and supercritical fluids", *Journal of Physical Organic Chemistry*, vol. 11, 1998, pp. 589-596.
Spilimbergo, S. et al., "Non-Thermal Bacterial Inactivation With Dense $CO_2$", *Biotechnology and Bioengineering*, vol. 84, No. 6, Dec. 20, 2003, pp. 627-638.

* cited by examiner

*Primary Examiner* — Devang Thakor

(74) *Attorney, Agent, or Firm* — McCarter & English, LLP; Matthew R. Van Eman

(57) ABSTRACT

Systems for sterilization of demineralized bone matrices are provided.

12 Claims, 6 Drawing Sheets

SYSTEMS AND METHODS FOR STERILIZATION OF BONE OR BONE COMPONENTS

This application claims priority under 35 U.S.C. §119 to U.S. Provisional Patent Application No. 61/258,487, which was filed on Nov. 5, 2009.

The present disclosure relates to the field of tissue sterilization.

Present methods for sterilization of tissues include gamma-irradiation, e-beam, and ethylene oxide (EO). Among them, gamma-irradiation and e-beam are known to alter the structure and characteristics of biomaterials through crosslinking and/or degradation of collagen matrix. EO sterilization typically operates at temperatures around 60° C., which is above the melting temperature of the collagen matrix in biological materials, such as, for example, dermal tissues. EO is also a recognized carcinogen, and its residual in biological materials can cause hemolysis and other toxic reactions. Further, gamma-irradiation and e-beam can eliminate or significantly reduce osteoinductivity of demineralized bone matrix.

Accordingly, there is a need for improved systems and methods for sterilization of tissues, including acellular tissue matrices.

This discussion of the background disclosure is included to place the present disclosure in context. It is not an admission that any of the background material previously described was published, known, or part of the common general knowledge at the priority date of the present disclosure and claims.

According to certain embodiments, a method of terminal sterilization is disclosed that includes treating a demineralized bone matrix in a supercritical carbon dioxide ($SC-CO_2$) chamber with a sterilant, wherein the demineralized bone matrix is osteoinductive after sterilization and storage for at least 12 months at ambient conditions.

According to certain embodiments, a dimineralized bone matrix is provided, wherein the demineralized bone matrix is produced by a method comprising treating the demineralized bone matrix with super critical $CO_2$ and a sterilant to sterilize the demineralized bone matrix, wherein the demineralized bone matrix is osteoinductive after sterilization and storage at ambient temperatures for at least 12 months.

DESCRIPTION OF EXEMPLARY EMBODIMENTS

Figure 1:
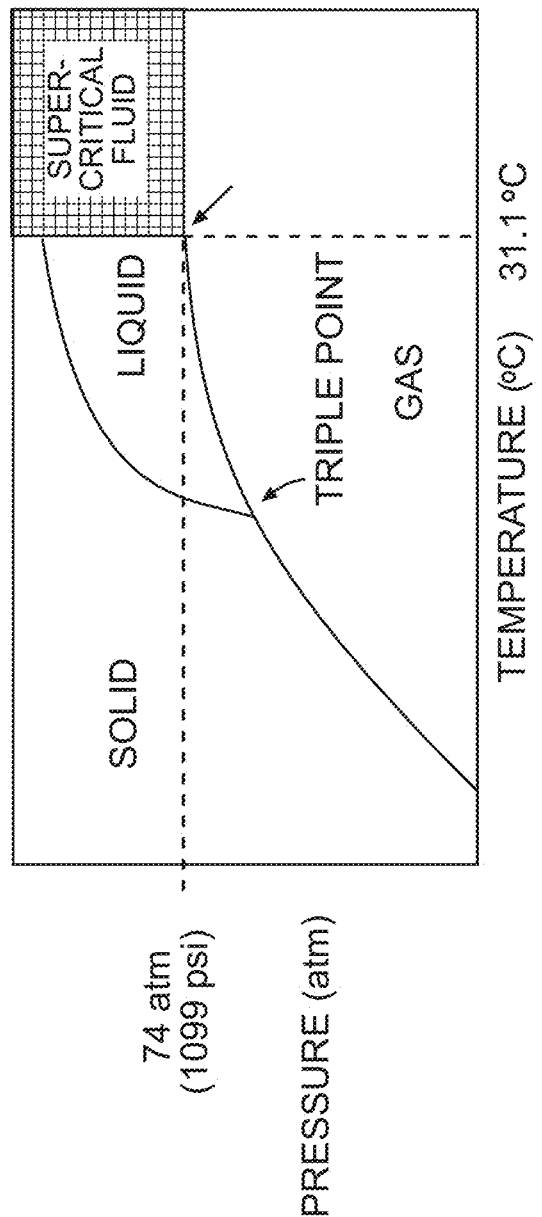
FIG. 1 is a phase diagram of $CO_2$.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit, unless specifically stated otherwise. Also, the use of the term "portion" may include part of a moiety or the entire moiety.

All documents, or portions of documents, cited in this application, including but not limited to patents, patent applications, articles, books, and treatises, are hereby expressly incorporated by reference in their entirety for any purpose.

The term "sterilization," as used herein, generally refers to the inactivation or elimination of viable microorganisms.

The term "bioburden," as used herein, generally refers to the number of contaminating microbes on a certain amount of material.

The term "tissue" will be understood to refer to intact tissue or components of tissues, including acellular tissue matrices.

The term "ambient conditions" will be understood to refer to temperatures ranging from 20-30° C. and conditions that are basically dry.

The present disclosure relates to systems and methods for sterilization of tissues. Some exemplary embodiments relate to sterilization using supercritical carbon dioxide ($SC-CO_2$). Supercritical carbon dioxide sterilization involves the use of $SC-CO_2$, alone or with the addition of one or more sterilants, for bioburden reduction. Supercritical carbon dioxide has unique properties that make it an appealing medium for sterilization. Its high diffusion characteristics allow for deep penetration into materials. In addition, it is nontoxic and can easily be removed by depressurization and out-gassing. Further, $SC-CO_2$ can be effective at inactivating a variety of microorganisms.

In some exemplary embodiments, $SC-CO_2$ may be used to sterilize bone or bone components. In certain embodiments, the bone or bone components include demineralized bone (DBM). In certain embodiments, the DBM is osteoinductive after sterilization. In certain embodiments, the DBM is stored in dry form to maintain osteoinductivity. In some embodiments, the DBM is dried before or after sterilization. Further, in certain embodiments, the DBM may be combined with one or more other materials, such as particulate or fibrous acellular soft tissues, including dermis. One such acellular soft tissue is CYMETRA®, which is a particulate acellular dermal material. Further, the DBM may be sterilized alone or when mixed with other materials. Particulate acellular tissues, DBM, combinations of DBM and other materials, and methods for freeze-drying and storing such materials are further described in U.S. Pat. No. 6,933,326 and US Patent Publication Numbers 2007/0248575 and 2003/0143207.

In some embodiments, the DBM, acellular tissue matrix, or combination thereof may be treated with $SC-CO_2$ and at least one sterilant, which can further enhance the inactivation of microbes. Such sterilants may include, for example, peracetic acid (PAA), which can be bactericidal, fungicidal, virucidal, and sporicidal. Use of a sterilant in conjunction with $SC-CO_2$, in various embodiments disclosed herein, may facilitate achieving industrial level sterilization with a Sterility Assurance Level of $10^{-6}$ (i.e., a probability of 1 in 1,000,000 of finding a non-sterile device). In some embodiments, combining $SC-CO_2$ with a sterilant may facilitate achieving industrial sterilization of DBM or DBM in combination with other materials without affecting the osteoinductivity of the DBM.

The DBM products discussed herein can be packaged in a variety of ways. For example, the products can be packaged using systems that permit sterilization using $SC-CO_2$ and a sterilant, but prevent contamination of samples after sterilization. In some embodiments, the products are sterilized and packaged using a packaging system having multiple components. For example, a suitable system can include an outer package having a first portion that is permeable to $SC-CO_2$ and a sterilant. The first portion can also be impermeable to bacteria and therefore will function as a sterile barrier. The outer package can also include a second portion that is impermeable to moisture. The second portion can be used to seal the package within a moisture tight enclosure subsequent to sterilization without transferring the device to a separate container. In some cases, the packaging will also include an inner package, which will be permeable to $SC-CO_2$ and a sterilant, and may comprise, for example, TYVEK®.

Exemplary Sterilization Process

In certain embodiments, super-critical carbon dioxide ($SC-CO_2$) can serve as an inert carrier for the delivery of sterilants. In some embodiments, the sterilants can include, peracetic acid (PAA) and/or hydrogen peroxide ($H_2O_2$). $SC-CO_2$ exhibits properties of both the gaseous and liquid physical states. It has the viscosity of a liquid and the transport efficiency of a gas which allow for efficient delivery with high penetration properties.

FIG. 1 displays the phase diagram for the conversion of $CO_2$ to the super-critical state. The super-critical state is a unique physical state that is achieved at a specific temperature and pressure combination defined as the "critical point". The super-critical state is absolute once the critical point is reached within the environment and the pressure and temperature are uniform throughout a super-critical environment.

In certain embodiments, during the sterilization process, the $CO_2$ is pumped into the chamber, and the pressure and temperature are modulated until the critical point is surpassed, yielding the super-critical state within the chamber. The pressure and temperature are monitored to maintain the required super-critical state pressure/temperature values for the duration of the processing run. If either the pressure or temperature range falls out of the required metric, the run is registered as a failure. The real-time measurements of the temperature and pressure values are recorded and can be produced as a hard-copy printout.

Figure 2:
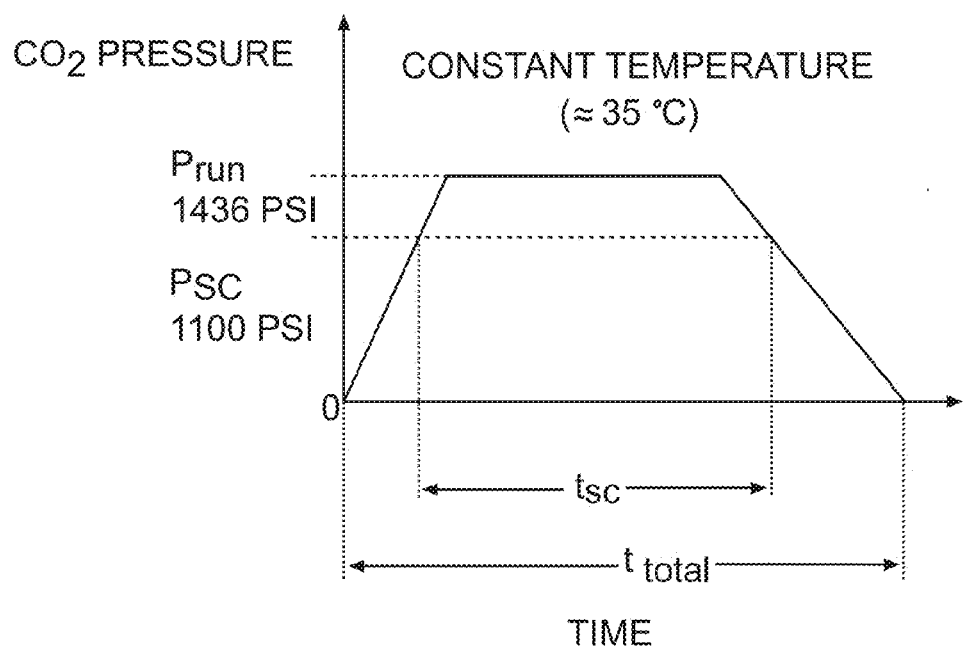
FIG. 2 is a diagram of process pressure vs. time flow, for a sterilization process, according to certain embodiments.
Figure 3:
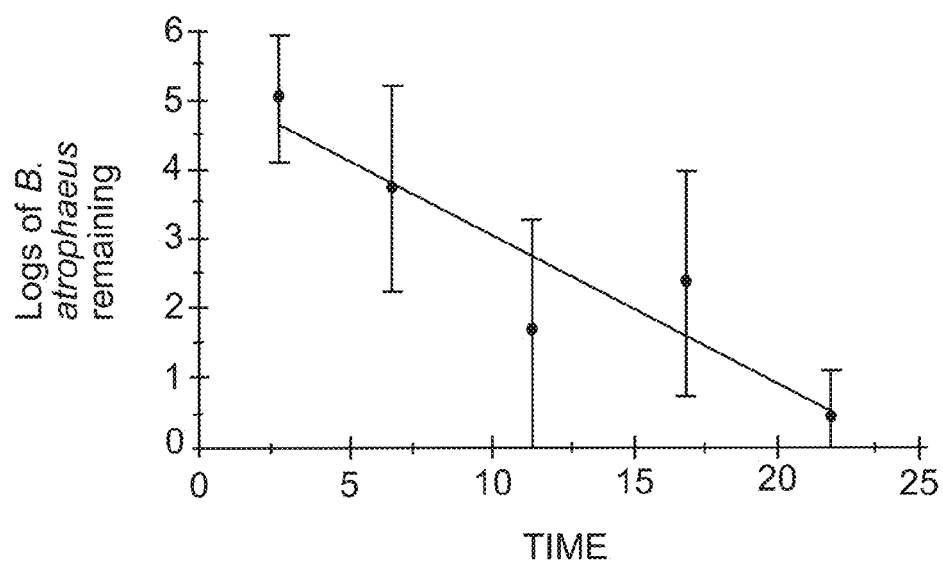
FIG. 3 is a log-kill plot of model resistant bioburden, according to certain embodiments.

FIG. 2 is a diagram of process pressure vs. time flow, according to certain embodiments. During the treatment process, an instrument provides heat to a treatment chamber to maintain a constant temperature of ~35° C., while the pressure is increased to above the critical point. Once the preset super-critical state (P=1346 psi, T=35° C.) is achieved, the sterilization time is initiated. In various embodiments, during the validated sterilization process, under super-critical conditions, both the pressure and temperature are constant. In some embodiments, the only variable for the sterilization process is the exposure time.

As FIG. 2 illustrates, there is a pre-sterilization time frame while the critical pressure is achieved. After that time, the pressure and temperature are held constant at values within the super-critical phase requirements. The sterilization time is then initiated, and the required exposure time is executed ($t_{sc}$). Following the completion of the sterilization exposure phase, the chamber pressure is reversed to allow retrieval of the sterile samples. The complete process of achieving the super-critical phase and its reversal are represented by the total process time ($t_{total}$).

Sterilant Components

The sterilant component of the sterilization system consists of a stock solution that contains PAA and $H_2O_2$ (Sigma Cat No #269336) that is diluted with sterile distilled water at the time of use. In some embodiments, the PAA and $H_2O_2$ in the sterilant have concentrations of 12%±2.0% and 2.0%±1.0% w/v, respectively. The working concentrations of PAA and $H_2O_2$ inside the sterilization chamber are about 54 ppm and 9 ppm, respectively. PAA and $H_2O_2$ working concentration ranges inside the chamber can be 1-1000 ppm and 1-1000 ppm, respectively. The preferred ranges are 20-100 ppm and 1-20 ppm.

At the onset of the sterilization process, the sterilant is placed into the $SC-CO_2$ chamber. The presence of PAA/$H_2O_2$ throughout the chamber can be confirmed by PAA and $H_2O_2$ test strips placed at different locations of the chamber during the IQ/OQ validation of the equipment. In various embodiments, the process can achieve $SAL=10^{-6}$ sterilization.

Example 1: Sterilization of Demineralized Bone Matrix

A non-conventional sterilization method that uses super-critical carbon dioxide with peracetic acid sterilant ($SC-CO_2$-PAA) has been developed, as described above. The purpose of this study was to investigate if this sterilization method can be used for demineralized bone matrix (DBM) without significantly affecting DBM's osteoinductivity. The DBM used in this study was from LifeLink Tissue Bank (Tempa, Fla.). Two lots of DBM dry particulates were sterilized using $SC-CO_2$-PAA, and their osteoinductivities were evaluated using a nude rat intramuscular implant model. The DBM particulates were stored in dry form during ambient storage.

Two lots of DBM particulates (labeled 366-45-1 and 366-45-2 in tables below) were packaged in Tyvek pouches (1.1-1.2 g/pouch) and then treated with $SC-CO_2$-PAA for 30 min (Run Time), using the concentrations and conditions described above, in the $SC-CO_2$ chamber (Nova 2200, NovaSterilis), NY After treatment, the samples were placed in a nitrogen atmosphere for 24 hours before being sealed in foil pouches. Untreated DBMs were used as controls.

Both lots of DBM were implanted intramuscularly in nude rats at time 0 to evaluate their osteoinductivity. Samples from the first lot (labeled 366-45-1 in the tables below) were also implanted intramuscularly into rats after 6 and 12 months ambient storage to evaluate osteoinductivity. Four rats were used to test samples from each lot. Untreated DBM was implanted intramuscularly at one control site for each rat (Tables 1A, 1B, and 1C).

TABLE 1A

Implantation of Test and Control Samples at Time 0

| Animal Number | Left Leg/Lot # | Right Leg/Lot # |
|---|---|---|
| 1-4 | 366-45-1 test | 366-45-1 control |
| 5-8 | 366-45-2 test | 366-45-2 control |

TABLE 1B

Implantation of Test and Control Samples at 6-month Ambient Storage

| Animal Number | Left Leg/Lot # | Right Leg/Lot # |
|---|---|---|
| 1-4 | 366-45-1 test | 366-45-1 control |

TABLE 1C

Implantation of Test and Control Samples at 12-month Ambient Storage

| Animal Number | Left Leg/Lot # | Right Leg/Lot # |
|---|---|---|
| 1-4 | 366-45-2 control | 366-45-2 test |

At 6 month and 12 month storage time points, approximately 250 mg of DBM was hydrated prior to the implantation. The hydrated DBM was then placed into a pocket created intramuscularly, and the muscular pocket and skin were closed. After 28 days, the animals were sacrificed, and the implant sites removed. The tissues were fixed in 10% neutral buffered formalin and were then processed for histologic evaluation. Sections were cut and stained with hematoxylin and eosin. Histological slides from the time 0 explants were examined under a microscope by a pathologist using the scoring system shown in Table 2.

TABLE 2

Criteria for Microscopic Evaluation of Osteoinduction per Implant Site Semi-Quantitative Analysis

| Grade | Estimated Cross-Section Area |
|---|---|
| 0 | 0%, No evidence of new bone formation |
| 1 | 1-25% of field shows evidence of new bone formation |
| 2 | 26-50% of field shows evidence of new bone formation |
| 3 | 51-75% of field shows evidence of new bone formation |
| 4 | 76-100% of field shows evidence of new bone formation |

The explants at the 6 and 12 month time points were divided into halves. One set was processed and evaluated by a pathology test facility using the scoring system shown in Table 2, and the other set was processed and evaluated blindly by an experienced scientist at LifeCell Corporation. All of the implant sites showed evidence of new bone formation, as summarized in Tables 3 and 4.

TABLE 3

Summary of Pathologist Results (AppTec)

| | | Scores | | |
|---|---|---|---|---|
| Lot # | Treatment | 0-month Average ± SD | 6-month Average ± SD | 12-month Average ± SD |
| 366-45-1 | Control | 2.0 ± 0.8 | 3.0 ± 0.0 | 1.0 ± 0.0 |
| | Treated | 1.5 ± 0.6 | 1.5 ± 0.6 | 1.0 ± 0.0 |

TABLE 4

Summary of Pathologist Results (LifeCell)

| | | % of new bone area | | |
|---|---|---|---|---|
| Lot # | Treatment | 0-month Average ± SD | 6-month Average ± SD | 12-month Average ± SD |
| 366-45-1 | Control | 25(±1)% | 34(±10)% | 24(±3)% |
| | Treated | 24(±1)% | 30(±1)% | 24(±4)% |

DBM can retain its osteoinductivity after sterilization with super-critical carbon dioxide and PAA sterilant, and no significant change in osteoinductivity was evident after 12-months ambient storage.

Figure 4:
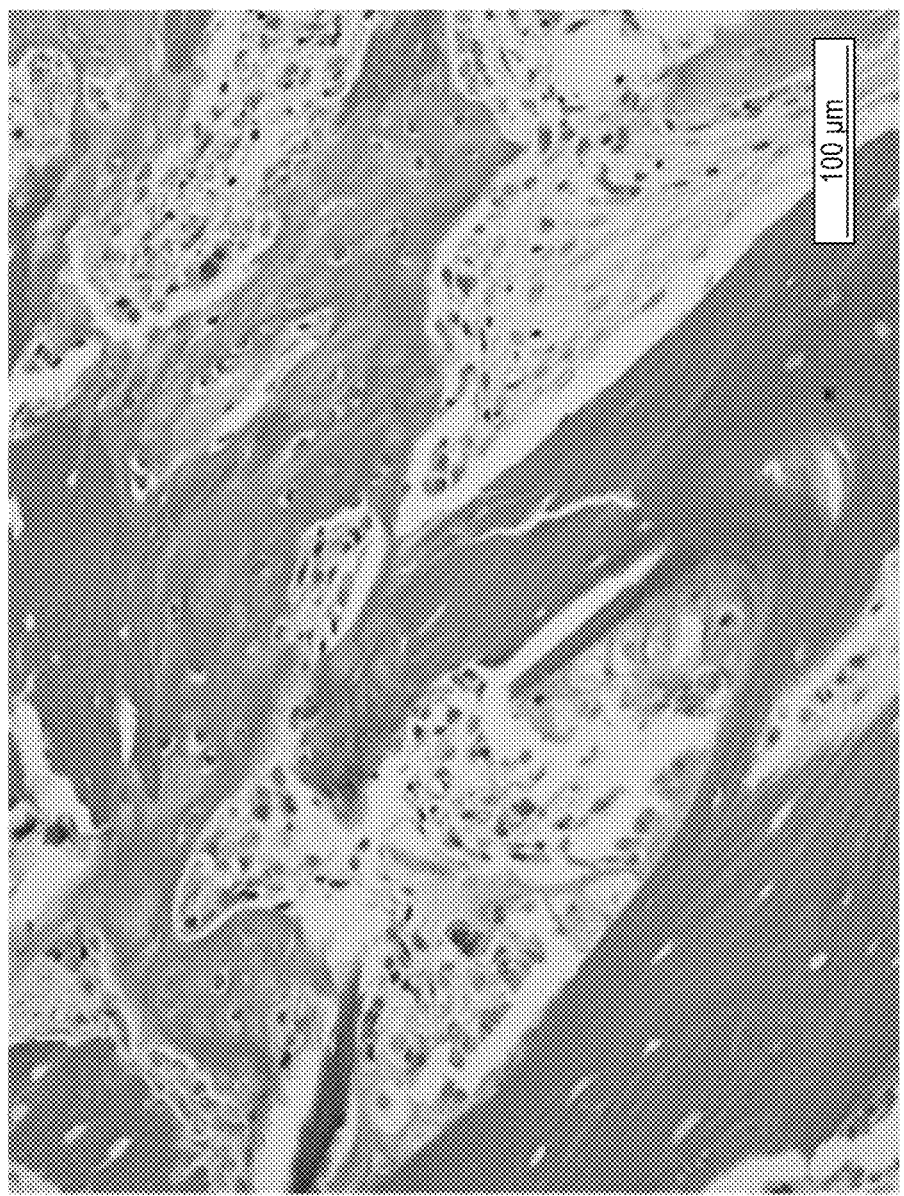
FIG. 4 is a photomicrograph of demineralized bone matrix after sterilization and storage for 6 months under ambient conditions, followed by intramuscular implantation within a rat, according to certain embodiments.
Figure 5:
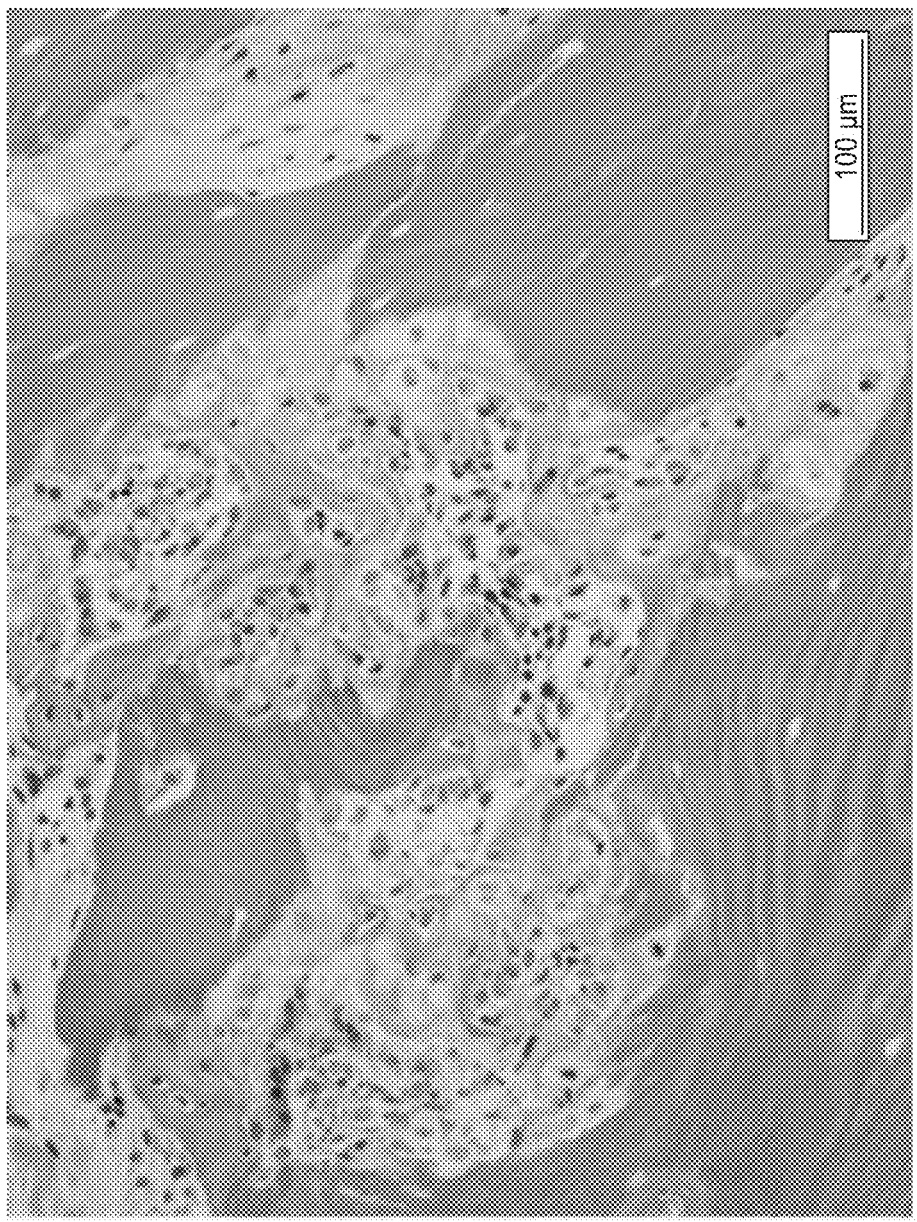
FIG. 5 is a photomicrograph of demineralized bone matrix after sterilization and storage for 6 months under ambient conditions, followed by intramuscular implantation within a rat, according to certain embodiments.
Figure 6:
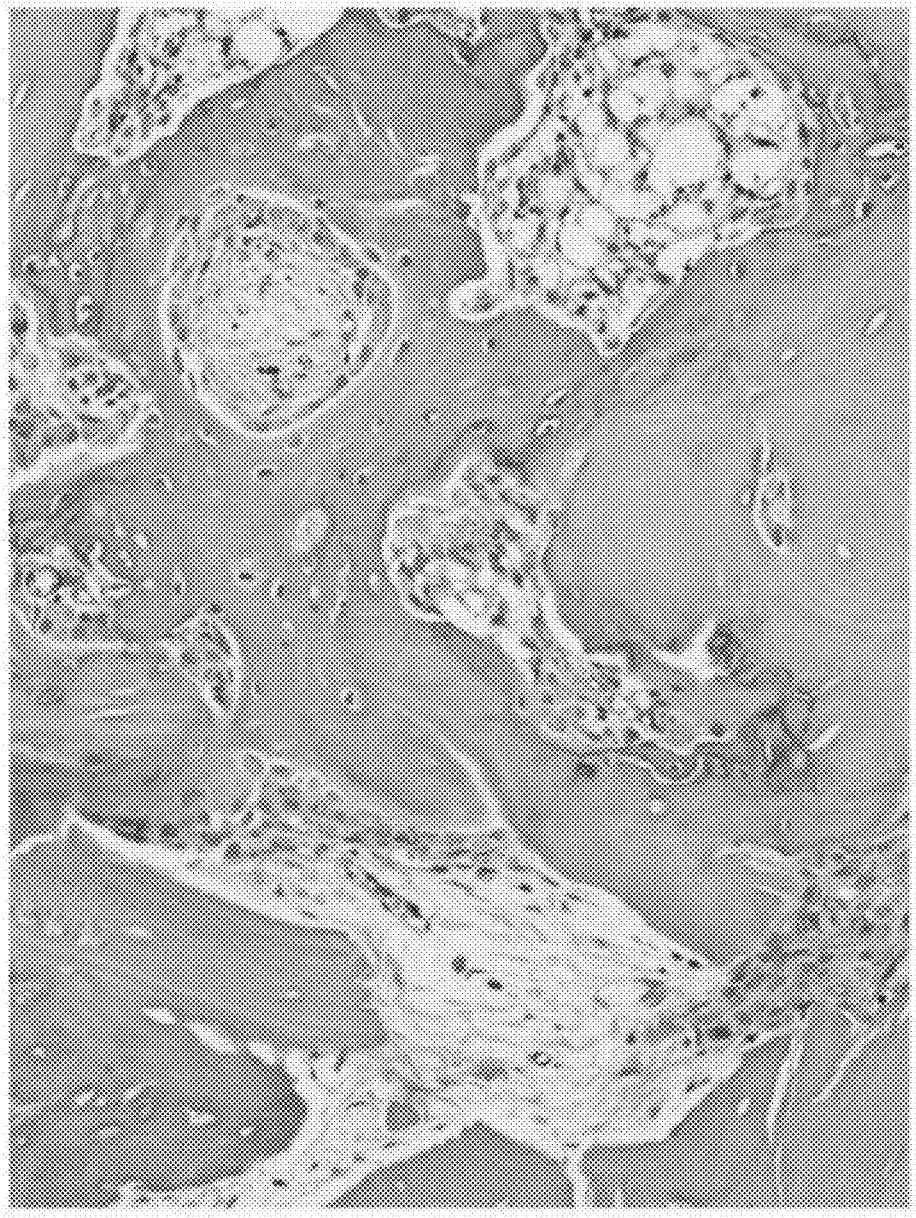
FIG. 6 is a photomicrograph of demineralized bone matrix after sterilization and storage for 12 months under ambient conditions, followed by intramuscular implantation within a rat, according to certain embodiments.
Figure 7:
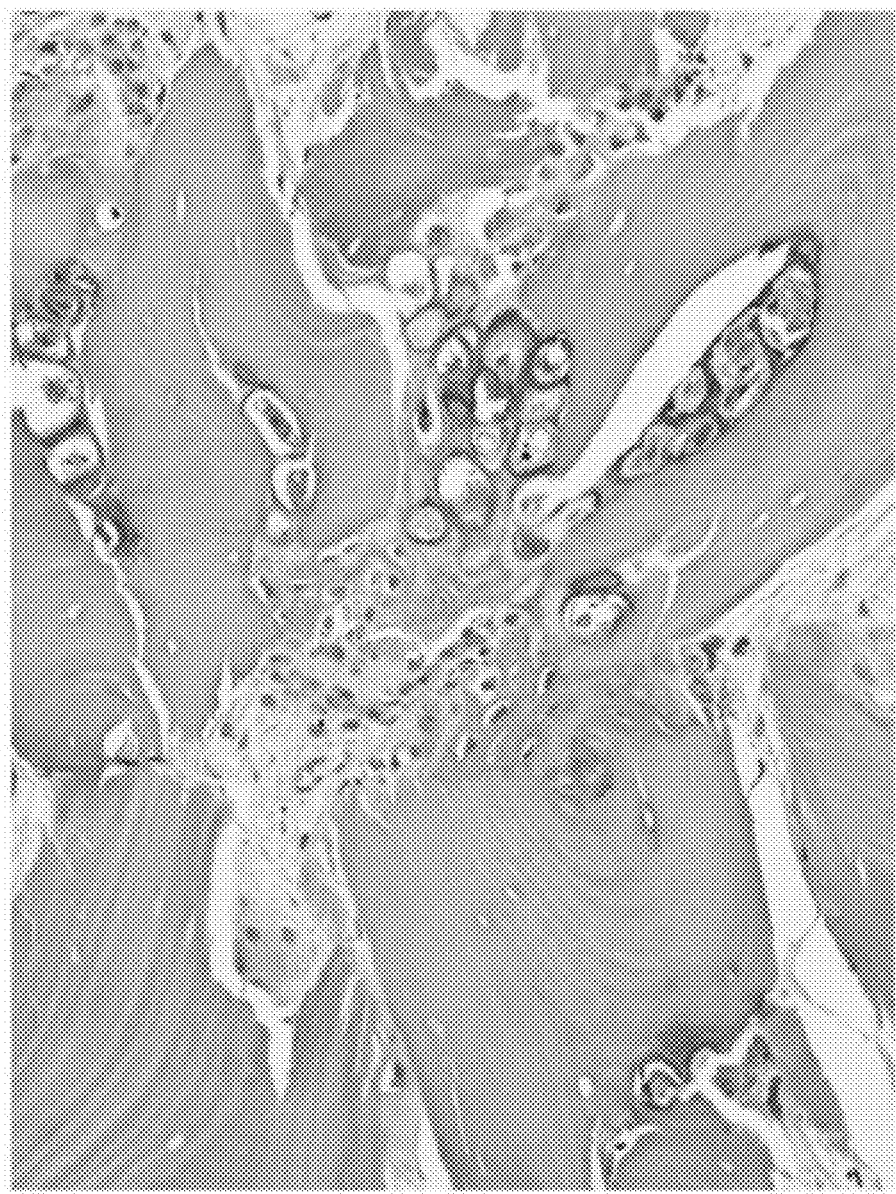
FIG. 7 is a photomicrograph of demineralized bone matrix after sterilization and storage for 12 months under ambient conditions, followed by intramuscular implantation within a rat, according to certain embodiments.

In addition, the light microscopy evaluations of samples after 6- and 12-months of storage are summarized in Tables 5A and 5B. Both tables include the average percent of field showing new bone formation for all animals. A 20X objective lens was used, and four fields on each slide were examined. The evaluator was blinded to the treatments. FIGS. 4 and 5 are representative photomicrographs of demineralized bone matrix that was implanted after being sterilized and stored for 6 months. FIG. 4 is the untreated control while FIG. 5 is the test sample. FIGS. 6 and 7 are representative micrographs after 12 months, with FIG. 6 as the test sample and FIG. 7 as the control. All micrographs show new bone formation.

TABLE 5A

Percent of Field Showing New Bone Formation After 6-Months Storage

| Sample ID* 2009H016 | 20× field-1 | 20× field-2 | 20× field-3 | 20× field-4 | Average |
|---|---|---|---|---|---|
| 1 | 30% | 25% | 25% | 30% | 28% |
| 2 | 20% | 30% | 30% | 20% | 25% |
| 3 | 50% | 25% | 20% | 30% | 31% |
| 4 | 60% | 50% | 50% | 30% | 48% |
| 5 | 45% | 35% | 20% | 20% | 30% |
| 6 | 30% | 30% | 30% | 30% | 30% |
| 7 | 50% | 35% | 25% | 15% | 31% |
| 8 | 50% | 25% | 30% | 25% | 33% |

Note:
Samples 1, 3, 5 and 7 are treated samples, and 2, 4, 6 and 8 are controls.

TABLE 5B

Percent of Field Showing New Bone Formation After 12-Months Storage

| Sample ID 2010H062 | Field-1 (%) | Field-2 (%) | Field-3 (%) | Field-4 (%) | Field-5 (%) | Field-6 (%) | Average (%) |
|---|---|---|---|---|---|---|---|
| 1L | 12.8 | 18.8 | 15.5 | 13.4 | 32.1 | 20.8 | 18.9 |
| 1R | 12.6 | 38.2 | 37.8 | 22.3 | 21.3 | 20.2 | 25.4 |
| 2L | 20.1 | 11.4 | 20.4 | 24.2 | 31.8 | 42.0 | 25.0 |
| 2R | 50.9 | 7.8 | 22.7 | 8.0 | 14.8 | 14.0 | 19.7 |
| 3L | 30.0 | 26.4 | 35.7 | 16.3 | 25.4 | 23.0 | 26.1 |
| 3R | 21.1 | 42.1 | 25.5 | 20.9 | 20.5 | 12.8 | 23.8 |
| 4L | 40.0 | 17.2 | 11.8 | 21.4 | 17.7 | 40.9 | 24.9 |
| 4R | 36.9 | 26.3 | 27.6 | 17.9 | 24.4 | 35.6 | 28.1 |

All the samples demonstrated new bone formation after storing the DBM for 6 or 12 months after sterilization. Most of the samples showed ~30% new bone growth at 6 months and ~25% at 12 months. Generally, the evidence of the new bone formation or potential new bone formation found in the samples included the presence of osteoid, osteoblasts/osteoclasts, calcified cartilage matrix/hypertrophic chondrocytes, bone marrow, clusters of chondroblasts/condrorocytes and some membrane-like connective tissue (FIGS. 4-7).

Other embodiments will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for sterilizing demineralized bone matrix, comprising:
    packaging the demineralized bone matrix in an inner package prior to treatment with super critical $CO_2$, the inner package being permeable to super critical $CO_2$ and a sterilant,
    packaging the inner package in an outer package prior to treatment with super critical $CO_2$, the outer package comprising (i) a first portion including a material that is permeable to super critical $CO_2$ and the sterilant, and (ii) a second portion that is impermeable to moisture,
    treating the demineralized bone matrix with super critical $CO_2$ and the sterilant to sterilize the demineralized bone matrix, and
    sealing the first portion of the outer package with the second portion of the outer package subsequent to sterilization such that the inner package is sealed within a moisture impermeable enclosure,
    wherein the demineralized bone matrix maintains osteoinductivity after sterilization and storage at ambient temperature for at least 12 months.

2. The method of claim 1, wherein the sterilant comprises peracetic acid (PAA).

3. The method of claim 2, wherein the sterilant further comprises a peroxide.

4. The method of claim 3, wherein the peroxide is $H_2O_2$.

5. The method of claim 4, wherein concentrations of PAA and $H_2O_2$ in the sterilant are 10-14% and 1-3%, respectively.

6. The method of claim 4, further comprising treating the demineralized bone matrix in a chamber, wherein concentrations of PAA and $H_2O_2$ in the chamber are 1-1000 ppm and 1-1000 ppm, respectively.

7. The method of claim 6, wherein the concentrations of PAA and $H_2O_2$ in the chamber are 20-100 ppm and 1-10 ppm, respectively.

8. The method of claim 1, wherein the demineralized bone matrix is sterilized when mixed with other materials.

9. The method of claim 1, wherein during the sterilization process, pressure and temperature are kept constant.

10. The method of claim 1, wherein after treatment with super critical $CO_2$, the demineralized bone matrix is placed in a nitrogen atmosphere for 0-24 hours.

11. The method of claim 1, further comprising mixing the demineralized bone matrix with a particulate acellular tissue matrix before or after sterilization.

12. A method for sterilizing demineralized bone matrix, comprising:
    packaging the demineralized bone matrix in an inner package prior to treatment with super critical $CO_2$, the inner package being permeable to super critical $CO_2$ and a sterilant,
    packaging the inner package in an outer package prior to treatment with super critical $CO_2$, the outer package comprising (i) a first portion including a material that is permeable to super critical $CO_2$ and the sterilant, and (ii) a second portion that is impermeable to moisture,
    treating the demineralized bone matrix with super critical $CO_2$ and the sterilant to sterilize the demineralized bone matrix,
    after treatment with super critical $CO_2$ and the sterilant, placing the demineralized bone matrix in a nitrogen atmosphere for 24 hours, and
    sealing the first portion of the outer package with the second portion of the outer package subsequent to sterilization such that the inner package is sealed within a moisture impermeable enclosure.

* * * * *